United States Patent
Wallen

(10) Patent No.: US 11,266,805 B2
(45) Date of Patent: Mar. 8, 2022

(54) ANESTHETIC BREATHING APPARATUS HAVING VOLUME REFLECTOR UNIT WITH CONTROLLABLE PENETRATION

(71) Applicant: MAQUET CRITICAL CARE AB, Solna (SE)

(72) Inventor: Lars Wallen, Spanga (SE)

(73) Assignee: MAQUET CRITICAL CARE AB, Solna (SE)

( * ) Notice: Subject to any disclaimer, the term of this patent is extended or adjusted under 35 U.S.C. 154(b) by 1407 days.

(21) Appl. No.: 14/844,544

(22) Filed: Sep. 3, 2015

(65) Prior Publication Data
US 2015/0374947 A1 Dec. 31, 2015

Related U.S. Application Data

(62) Division of application No. 13/320,489, filed as application No. PCT/EP2009/055789 on May 13, 2009, now Pat. No. 9,149,590.

(51) Int. Cl.
*A61M 16/10* (2006.01)
*A61M 16/00* (2006.01)
(Continued)

(52) U.S. Cl.
CPC ...... *A61M 16/104* (2013.01); *A61M 16/0051* (2013.01); *A61M 16/01* (2013.01);
(Continued)

(58) Field of Classification Search
CPC .............. A61M 16/00; A61M 16/0003; A61M 16/0045; A61M 16/0051;
(Continued)

(56) References Cited

U.S. PATENT DOCUMENTS

| 4,989,597 A | * | 2/1991 | Werner | ............... A61M 16/104 128/203.12 |
| 5,471,979 A | | 12/1995 | Psaros et al. | |

(Continued)

FOREIGN PATENT DOCUMENTS

| CN | 1246372 A | 3/2000 |
| WO | 2007/065476 A1 | 6/2007 |

(Continued)

OTHER PUBLICATIONS

International Search Report dated Feb. 10, 2010 for International Application No. PCT/EP2009/055789.
(Continued)

*Primary Examiner* — Rachel T Sippel

(57) ABSTRACT

An anesthetic breathing apparatus and system, having a patient circle system for re-breathing exhaled gases by a patient a volume reflector, a fresh gas delivery line, and a gas sensor unit arranged to measure a gas stream upstream a fresh gas connection and downstream said reflector unit. The gas sensor unit provides a signal for detection of a reflector driving gas (RDG) crossing over the volume reflector during inspiration based on at least one property of the gas stream measured by the gas sensor unit. Appropriate action may be taken based on this measurement, for instance in disclosed methods.

34 Claims, 7 Drawing Sheets

(51) Int. Cl.
*A61M 16/08* (2006.01)
*A61M 16/01* (2006.01)
*A61M 16/22* (2006.01)
*A61M 16/18* (2006.01)

(52) U.S. Cl.
CPC ....... *A61M 16/0891* (2014.02); *A61M 16/009* (2013.01); *A61M 16/18* (2013.01); *A61M 16/22* (2013.01); *A61M 2016/003* (2013.01); *A61M 2016/0027* (2013.01); *A61M 2016/102* (2013.01); *A61M 2202/0208* (2013.01); *A61M 2202/0241* (2013.01); *A61M 2205/15* (2013.01); *A61M 2205/18* (2013.01); *A61M 2205/3334* (2013.01); *A61M 2205/50* (2013.01); *A61M 2205/502* (2013.01)

(58) Field of Classification Search
CPC .... A61M 16/0057–0084; A61M 16/01; A61M 16/0891; A61M 16/10–104; A61M 16/105–107; A61M 16/12; A61M 16/18; A61M 16/22
See application file for complete search history.

(56) References Cited

U.S. PATENT DOCUMENTS

| | | | | |
|---|---|---|---|---|
| 5,857,458 | A * | 1/1999 | Tham | A61M 16/10 |
| | | | | 128/203.12 |
| 6,095,137 | A * | 8/2000 | Wallroth | A61M 16/01 |
| | | | | 128/203.26 |
| 6,131,571 | A * | 10/2000 | Lampotang | A61M 16/0833 |
| | | | | 128/204.21 |
| 7,024,945 | B2 * | 4/2006 | Wallace | A61M 16/024 |
| | | | | 73/861.74 |
| 7,438,072 | B2 | 10/2008 | Izuchukwu | |
| 2004/0149281 | A1 * | 8/2004 | Ahlmen | A61M 16/1065 |
| | | | | 128/203.12 |
| 2005/0133024 | A1 * | 6/2005 | Coifman | A61B 5/087 |
| | | | | 128/200.14 |
| 2008/0029092 | A1 * | 2/2008 | Heesch | A61M 16/10 |
| | | | | 128/203.14 |
| 2008/0202526 | A1 * | 8/2008 | Heinonen | A61M 16/0051 |
| | | | | 128/204.22 |
| 2008/0264417 | A1 * | 10/2008 | Manigel | A61M 16/01 |
| | | | | 128/204.21 |
| 2008/0289628 | A1 * | 11/2008 | Hallback | A61B 5/0813 |
| | | | | 128/203.12 |
| 2009/0277448 | A1 | 11/2009 | Ahlmen et al. | |
| 2010/0252046 | A1 | 10/2010 | Dahlstrom et al. | |
| 2010/0307490 | A1 | 12/2010 | Broborg et al. | |
| 2011/0000488 | A1 | 1/2011 | Blomberg | |
| 2011/0000489 | A1 * | 1/2011 | Laksov | A61B 5/0488 |
| | | | | 128/204.23 |
| 2011/0168177 | A1 * | 7/2011 | Connor | A61M 16/01 |
| | | | | 128/203.14 |
| 2015/0083121 | A1 * | 3/2015 | Fisher | A61M 16/024 |
| | | | | 128/202.22 |

FOREIGN PATENT DOCUMENTS

| | | |
|---|---|---|
| WO | 2007/071756 A1 | 6/2007 |
| WO | 2009/006932 A1 | 1/2009 |
| WO | 2009/062540 A1 | 5/2009 |
| WO | 2009/062547 A1 | 5/2009 |
| WO | 2009062540 A1 | 5/2009 |
| WO | 2009062547 A1 | 5/2009 |

OTHER PUBLICATIONS

European Search Report and Written Opinion issued in European Application No. 14156677.8 dated Aug. 22, 2014, 5 pages.

* cited by examiner

ANESTHETIC BREATHING APPARATUS HAVING VOLUME REFLECTOR UNIT WITH CONTROLLABLE PENETRATION

RELATED APPLICATION

The present application is a divisional application of U.S. application Ser. No. 13/320,489, filed Feb. 6, 2012, the contents of which are incorporated herein by reference.

BACKGROUND OF THE INVENTION

Field of the Invention

This invention pertains in general to the field of anesthetic breathing apparatuses having a volume reflector unit for providing gas from a reflector volume thereof re-entering into a breathing circuit during inspiration.

Description of the Prior Art

In inhalational anesthesia, anesthetic reflectors for the reflection of unused, gas born, anesthetic agents in expiration gas back towards a patient.

For instance in U.S. Pat. No. 4,989,597, an exchanger for open separation is disclosed. The exchanger directly interfaces a ventilator to a patient breathing circuit, and comprises a long, convoluted tube having a narrow diameter, yet large total volume. The open separation of the gases is resulting from the long mixing tube, which contains a volume of two to three liters of gas. There is no divider, such as a filter or membrane, such as in a traditional bag in bottle system, between the separated gas columns of the ventilator and the patient circuit.

The large exchanger tube volume is used as a reflector volume which is connected to the patient circuit via a first outlet/inlet port for receiving gas from the patient circuit during expiration, and for providing gas from the reflector volume into the breathing circuit during inspiration. Further, the reflector unit has an opposite inlet/outlet port which connects the reflector volume to an evacuation line via the ventilator during expiration, and to the ventilator as a controlled source of driving gas during inspiration.

This arrangement allows using the reflector volume with a driving gas pillar virtually moving back and forth in the reflector volume. In this manner an adjacent patient gas pillar alternatingly virtually is moving out of the patient circuit into the reflector volume during exhalation, and back into the patient circuit from the reflector volume during inspiration. Compared to a bag in bottle system, ventilation parameters are improved as there is no interfering membrane between the driving gas and the patient circuit.

In more detail, the reflector volume is thus cyclically filled with previously exhaled gas comprising an anesthetic gas (Xenon) is thus returned to the patient circuit for re-use during a subsequent inspiration. The driving gas, usually oxygen or air, is used as a driving gas pillar pushing the patient gas pillar back into the patient circuit during inspiration. Upon the subsequent expiration, the reflector volume is re-filled with expiratory gas and the driving gas pillar is pushed out of the reflector volume towards evacuation.

The patient gas column and the driving gas column may get admixed, e.g. due to turbulent flow. Furthermore, gas leakage may occur, e.g. leakage at a tracheal tube, or other locations in the anesthetic breathing apparatus.

These factors, singly or in combination, may lead to the driving gas column entering the patient circuit during inspiration. This crossing of the reflector driving gas over the volume reflector is called break-through or penetration of driving gas through the reflector unit and is an undesired condition, as the patient may receive less anesthetic agent than needed. This reduces patient safety as desired clinical effects to be obtained by the anesthetic agent may not be achieved.

In the anesthetic breathing apparatus of U.S. Pat. No. 4,989,597, an admixture of the gas columns occurs in the exchanger. An appropriate concentration of anesthetic gas is maintained by delivery of excess anesthetic gas in the breathing circuit as a compensation for losses due to mixing with the ventilator gas column.

This compensation is made to ensure the intended delivery of anesthetic gas, as even a small amount of mixing of the driving gas into the breathing circuit is regarded as undesired. Awakening or awareness of the patient may occur during anesthesia, which is highly undesired. In order to avoid this dire consequence, the excess amount of anesthetic gas is in U.S. Pat. No. 4,989,597 during every single exhalation wasted into the evacuation.

There is a need to avoid such losses of anesthetic gas from the breathing circuit, e.g. due to economic reasons.

The exchanger in the system disclosed in U.S. Pat. No. 4,989,597 is a long, narrow, convoluted tube having a reflector volume of 2-3 liters.

There is also a need to reduce the reflector volume, e.g. due to limited space when wanting to integrate the reflector volume in an anesthesia machine. Another reason for desired reduced reflector volumes is that ventilatory performance of the anesthetic breathing apparatus would be improved. A compressible reflector volume of 2-3 liters constitutes a large compressible volume that causes delays and is a source of inaccurate ventilatory regulation. It should be kept in mind that the tidal volume for an average grown up is approximately 0.5 liters. For children the tidal volumes may be lower than 100 ml. With regard to such comparatively low tidal volumes, a compressible volume of 2-3 liters is disadvantageous for ventilatory regulation.

Moreover, a well-defined front of the gas pillars requires a narrow tube or channel for the reflector volume, which consequently increases gas flow resistance, which is undesired. Increased resistance results e.g. in increased work of breathing of the patient during expiration, or leads to incomplete discharging of the patient's lungs during expiration.

However, reducing the reflector volume to a volume corresponding to a tidal volume, or less, raises other issues, as it would e.g. amplify the losses of anesthetic gas. Also, a reduced reflector volume entails narrower limits when leakage occurs, or when a patient requires large tidal volumes. The reflector volume is simply not sufficient for the task.

Hence, it would be advantageous to provide an improved anesthetic breathing apparatus having a reflector unit, allowing for reduced reflector volume, while maintaining or improving patient safety.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing an anesthetic breathing apparatus, a method, and a computer program product according to the appended patent claims.

According to a first aspect of the invention, an anesthetic breathing apparatus is provided, having a patient circle system for re-breathing exhaled gases by a patient. The apparatus comprises a volume reflector unit arranged in a common expiration and inspiration line and is connected to the patient circle system at a reflector connection. The apparatus further comprises a fresh gas delivery line connected to the patient circuit at a fresh gas connection, wherein the fresh gas connection is arranged downstream the reflector connection in the patient circle system. Further, the apparatus comprises a gas sensor unit that is arranged to measure at least one property of the gas stream upstream the fresh gas connection and downstream the reflector unit. The gas sensor unit is adapted to provide a signal for detection of a reflector driving gas (RDG) crossing over the volume reflector during inspiration based on the at least one property of the gas stream measured by the gas sensor unit.

The apparatus includes a control unit configured to detect a reflector driving gas (RDG) crossing over the volume reflector during inspiration, based on the at least one property of the gas stream measured by the gas sensor unit.

According to a second aspect of the invention, a method is provided for detecting a reflector driving gas (RDG) crossing over a volume reflector into a circle system in an anesthetic breathing apparatus, such as of the first aspect of the invention. The method comprises measuring at least one property of a gas stream upstream a fresh gas connection and downstream a reflector unit by means of a gas sensor unit, and detecting the reflector driving gas (RDG) crossing over the volume reflector during an inspiration phase, based on the at least one property of the gas stream measured by the gas sensor unit.

According to a third aspect of the invention, a non-transitory computer-readable storage medium is provided that is encoded with programming instructions (control commands) for detecting a reflector driving gas (RDG) crossing over a volume reflector in an anesthetic breathing apparatus, such as of the first aspect of the invention, for processing by a computer. The programming instructions include code segments, including a code segment for measuring at least one property of a gas stream upstream a fresh gas connection and downstream a reflector unit by means of a gas sensor unit, and a code segment for detecting the reflector driving gas (RDG) crossing over the volume reflector during an inspiration phase, based on the at least one property of the gas stream measured by the gas sensor unit.

According to a fourth aspect of the invention, a system is provided for controlling admixing of reflector driving gas (RDG) crossing over a volume reflector into a patient circle system in an anesthetic breathing apparatus, such as of the first aspect of the invention, is provided. The apparatus comprises the patient circle system for re-breathing exhaled gases by a patient, a volume reflector unit arranged in a common expiration and inspiration line and distally connected to the patient circle system at a reflector connection, and a fresh gas delivery line connected to the patient circuit at a fresh gas connection, wherein the fresh gas connection is arranged downstream the reflector connection in the patient circle system, and a gas sensor unit arranged to measure at least one property of the gas stream upstream the fresh gas connection and downstream the reflector unit and is adapted to provide a signal for detection of a reflector driving gas (RDG) crossing over the volume reflector during inspiration based on the at least one property of the gas stream measured by the gas sensor unit; and a control unit adapted to detect a reflector driving gas (RDG) crossing over the volume reflector during inspiration based on the at least one property of the gas stream measured by the gas sensor unit; wherein the control unit further is adapted to set operational modes of the anesthetic breathing apparatus.

The set operational mode comprises for instance, a controlled admixture of reflector driving gas into the patient circle system; delivery of a fresh gas composition via the fresh gas connection adapted to detected reflector driving gas entering the patient circle system; an increased anesthetic agent concentration to compensate for dilution by non re-breathed reflector driving gas entering the circle via the reflector connection; or an adapted re-breathing fraction based on the detected reflector driving gas crossing over the volume reflector.

According to a further aspect of the invention, a method of internally controlling admixing of reflector driving gas (RDG) crossing over a volume reflector into a circle system in a system of sixth aspect of the invention, is provided. The method comprises setting an operational mode of an anesthetic breathing apparatus upon detecting a reflector driving gas (RDG) crossing over a volume reflector during inspiration based on at least one property of the gas stream measured by the gas sensor unit.

Further embodiments of the invention are defined in the dependent claims, wherein features for the second and subsequent aspects of the invention are as for the first aspect mutatis mutandis.

Some embodiments of the invention provide for controlled reflector driving gas (RDG) crossing a volume reflector into a circuit system.

Some embodiments of the invention provide for increased safety of the anesthetic breathing apparatus while not increasing cost.

Some embodiments of the invention provide for advantageous ventilation of a patient. Advanced mechanical ventilation forms may be used in such an anesthetic breathing apparatus with maintained economical use of anesthetic agent.

Some embodiments of the invention provide for inspiratory ventilation of the patient with sufficient anesthetic agent, as desired by the user, at all times.

Some embodiments of the invention provide for anesthetic breathing apparatus having a volume reflector and a compact design.

Some embodiments of the invention also provide for increased patient safety as delivery of sufficient oxygen is provided to the patient and hypoxia is effectively avoided.

Some embodiments of the invention also provide for improved ventilatory performance of an anesthetic breathing apparatus as a compressible volume and flow resistance is kept low in a volume reflector provided.

The gas sensor unit may be based on measuring one or more properties of a gas or gas stream, such as a physical property or characteristic of said gas. The property is a detectable entity to provide reliable information concerning the presence or absence of a gas, directly or indirectly. For instance one or more of the following physical properties of said gas may be measured: heat conductivity, light absorption, paramagnetic properties, sound propagation speed in said gas, density of said gas, Doppler shift of a sound wave in said gas, molecular weight of said gas, etc. In some embodiments, a flow of said gas is such a property of said gas stream. In some embodiments, such a property of said gas is a gas flow related property of said gas stream, such as displaced volume. From gas flow, other entities may be calculated, such as flow rate, or gas volume displaced during a time period.

It should be emphasized that the term "comprises/comprising" when used in this specification indicates the presence of stated features, integers, steps or components but does not preclude the presence or addition of one or more other features, integers, steps, components or groups thereof.

In accordance with a first non-limiting illustrative embodiment of this disclosure, a system for detecting breathing circuit leakage in a volume reflector anesthesia breathing circuit is provided that comprises a control computer, and a gas sensor unit adapted to measure one or more properties of a gas or gas stream, the control computer configured to calculate a leakage volume based on at least one property of the gas or gas stream measured by the gas sensor unit in the volume reflector breathing circuit and to generate and emit an electrical signal representing the calculated leakage volume.

In accordance with a second non-limiting illustrative embodiment of this disclosure, the first non-limiting embodiment is modified so that the gas sensor unit is connected to a patient circle system and to a volume reflector in the breathing circuit. In accordance with a third non-limiting illustrative embodiment of this disclosure, the first non-limiting embodiment is modified so that the control computer is configured to calculate the leakage volume based on the volume of the gas stream measured by the gas sensor unit. In accordance with a fourth non-limiting illustrative embodiment of this disclosure, the third non-limiting embodiment is further modified so that the control computer is configured to calculate the leakage volume based on a difference of an inspiratory gas volume measured by the gas senor unit comprising a volume leaving the volume reflector during inspiration and a volume entering the volume reflector during the preceding expiration. In accordance with a fifth non-limiting illustrative embodiment of this disclosure, the third non-limiting embodiment is further modified so that the control computer is configured to provide, dependent on the calculated leakage volume, an indication or warning that reflector driving gas is crossing over the volume reflector.

In accordance with a sixth non-limiting illustrative embodiment of this disclosure, the first non-limiting embodiment is modified so that the control computer is configured to provide information related to leakage volume in the electrical signal. In accordance with a seventh non-limiting illustrative embodiment of this disclosure, the first non-limiting embodiment is modified so that the gas sensor unit is a gas sensor that measures absolute or relative concentration of at least one specific gas component. In accordance with an eighth non-limiting illustrative embodiment of the disclosure, the first non-limiting embodiment is modified so that the gas sensor unit is connected to a volume reflector in the breathing circuit, and wherein the gas sensor unit is configured to measure the property of gas flow at a measurement position thereof, the gas flow measurement being unidirectional or dependent on at least one of a direction of the gas flow out of the volume reflector and into the volume reflector. In accordance with a ninth non-limiting illustrative embodiment of this disclosure, the eighth non-limiting embodiment is further modified so that the gas sensor unit is a gas flow sensor arranged to measure differential pressure drop over a defined distance in a gas line at the measurement position.

In accordance with a tenth non-limiting illustrative embodiment of this disclosure, the first non-limiting embodiment is modified so that the gas sensor unit is an ultrasonic gas flow sensor that makes time of flight measurements to provide a signal for gas flow measurements, and measured ultrasonic sound propagation speed, at zero flow, as a measure of gas concentration or gas presence detection. In accordance with an eleventh non-limiting illustrative embodiment of the disclosure, the tenth non-limiting embodiment is further modified so that the gas senor unit is configured to measure a molecular weight of gases measured by measuring the ultrasonic sound propagation speed.

In accordance with a twelfth non-limiting illustrative embodiment of this disclosure, the first non-limiting embodiment is modified so that the gas sensor unit is configured to only detect relative changes of a concentration of a predetermined gas, and to detect relative gas composition changes during an inspiratory phase. In accordance with a thirteenth non-limiting illustrative embodiment of this disclosure, the twelfth non-limiting embodiment is further modified so that the gas sensor unit is connected to a volume reflector in the breathing circuit, and wherein the gas sensor unit is adapted to detect a change in carbon dioxide presence, or an absence of carbon dioxide, as a measure for reflector driving gas crossing the volume reflector.

In accordance with a fourteenth non-limiting illustrative embodiment of this disclosure, the first non-limiting embodiment is modified so that the gas sensor unit is arranged in the anesthetic breathing circuit to measure at least one property of the gas stream upstream a fresh gas connection and downstream a reflector unit of the anesthetic breathing circuit, and is configured to provide a signal allowing detection of a reflector driving gas crossing over the volume reflector during inspiration based on the at least one property of the gas stream measured by the gas sensor unit. In accordance with a fifteenth non-limiting illustrative embodiment of this disclosure, the first non-limiting embodiment is modified so that the gas sensor unit is fluidly connected to and arranged upstream of a junction in the breathing circuit where a fresh gas supply branch line joins a circle system. In accordance with a sixteenth non-limiting illustrative embodiment of this disclosure, the fifteenth non-limiting embodiment is further modified so that the gas sensor unit is fluidly connected to and arranged downstream of a junction in the breathing circuit where a driving gas line joints a volume reflector.

In accordance with a seventeenth non-limiting illustrative embodiment of this disclosure, the first non-limiting embodiment of this disclosure is modified so that the gas sensor unit is connected to a volume reflector in the breathing circuit, and wherein the gas sensor unit is fluidly connected to and arranged upstream of a junction in the breathing circuit where a fresh gas supply branch line joins a circle system, and wherein the gas sensor unit is arranged at a position selected from the group consisting of a position upstream of a carbon dioxide absorber unit and downstream of the volume reflector in a common line, and a position downstream of a junction where the reflector joins the circle system. In accordance with an eighteenth non-limiting illustrative embodiment of the disclosure, the seventeenth non-limiting embodiment is further modified so that the gas sensor unit is arranged upstream the junction where the reflector joins the circle system and is configured to measure flow or concentration related to reflector driving gas detection only during inspiration, and wherein an additional expiratory flow meter measures expiratory flow. In accordance with a nineteenth non-limiting illustrative embodiment of the disclosure, the seventeenth non-limiting embodiment is further modified so that the sensor unit is arranged upstream of the junction where the reflector joins the circle system and downstream of the carbon dioxide absorber unit, but upstream of the junction where the fresh gas supply branch line joins the circle system.

In accordance with a twentieth non-limiting illustrative embodiment, the seventeenth non-limiting embodiment is further modified so that the gas sensor unit is arranged to measure at least one property of the gas stream upstream of the fresh gas connection or upstream of the junction where the fresh gas supply branch line joins the circle system, and downstream the volume reflector, wherein the property of the gas stream is directly or indirectly related to the composition of the gas. In accordance with a twenty-first non-limiting illustrative embodiment of the disclosure, the twentieth non-limiting embodiment is further modified so that the gas sensor unit is configured to analyze the gas composition present between the volume reflector and an inspiratory limb of the anesthetic breathing circuit.

In accordance with a twenty-second non-limiting illustrative embodiment of the disclosure, the first non-limiting embodiment is modified so that the control computer is configured to set operational modes of an anesthetic breathing apparatus that comprises the breathing circuit, for controlling admixture of reflector driving gas into a patient circle system of the anesthetic breathing circuit. In accordance with a twenty-third non-limiting illustrative embodiment of the disclosure, the first non-limiting embodiment is modified so that the sensor unit is a unit selected from the group consisting of a gas identification unit, a gas concentration measurement unit, and a gas flow measurement unit. In accordance with a twenty-fourth non-limiting illustrative embodiment of the disclosure, the first non-limiting embodiment is modified so that the gas sensor unit is configured to measure a physical property that designates a presence or absence of a gas, directly or indirectly. In accordance with a twenty-fifth non-limiting illustrative embodiment of the disclosure, the twenty-fourth embodiment is further modified so that the gas sensor unit is configured to measure at least one of heat conductivity of the gas, light absorption of the gas, paramagnetic properties of the gas, sound propagation speed in the gas, density of the gas, Doppler shift of a sound wave in the gas, and molecular weight of the gas. In accordance with a twenty-sixth non-limiting illustrative embodiment of the disclosure, the twenty-fourth non-limiting embodiment is further modified so that the gas sensor unit is configured to measure at least one of a flow of the gas as property of the gas stream; a gas flow-related property of the gas stream, and flow rate or gas volume displaced during a time period calculated from the gas flow.

In accordance with a twenty-seventh non-limiting illustrative embodiment of this disclosure, a method is provided for detecting breathing circuit leakage in a patient circle system in an anesthetic breathing apparatus, the method comprising the steps of measuring at least one property of a gas stream by means of a gas sensor unit, and detecting the reflector driving gas crossing over the volume reflector during an inspiration phase, based on the at least one property of the gas stream measured by the gas sensor unit and further calculating a leakage volume based on the at least one property of the gas or gas stream measured by the gas sensor unit. In accordance with a twenty-eighth non-limiting illustrative embodiment of the disclosure, the twenty-seventh non-limiting embodiment is modified so that the method further comprises measuring the at least one property of the gas stream upstream a fresh gas connection and downstream a reflector unit of the anesthetic breathing apparatus.

In accordance with a twenty-ninth non-limiting illustrative embodiment of the disclosure, a non-transitory, computer-readable storage medium is provided encoded with programming instructions is provided for detecting breathing circuit leakage in a patient circle system in an anesthetic breathing apparatus, the storage medium being loaded into a computer and the programming instructions causing the computer to: receive a measurement of at least one property of a gas stream by means of a gas sensor unit; detect the reflector driving gas crossing over the volume reflector during an inspiration phase, based on the at least one property of the gas stream measured by the gas sensor unit; and calculate a leakage volume based on the at least one property of the gas or gas stream measured by the gas sensor unit.

DESCRIPTION OF THE PREFERRED EMBODIMENTS

Figure 1:
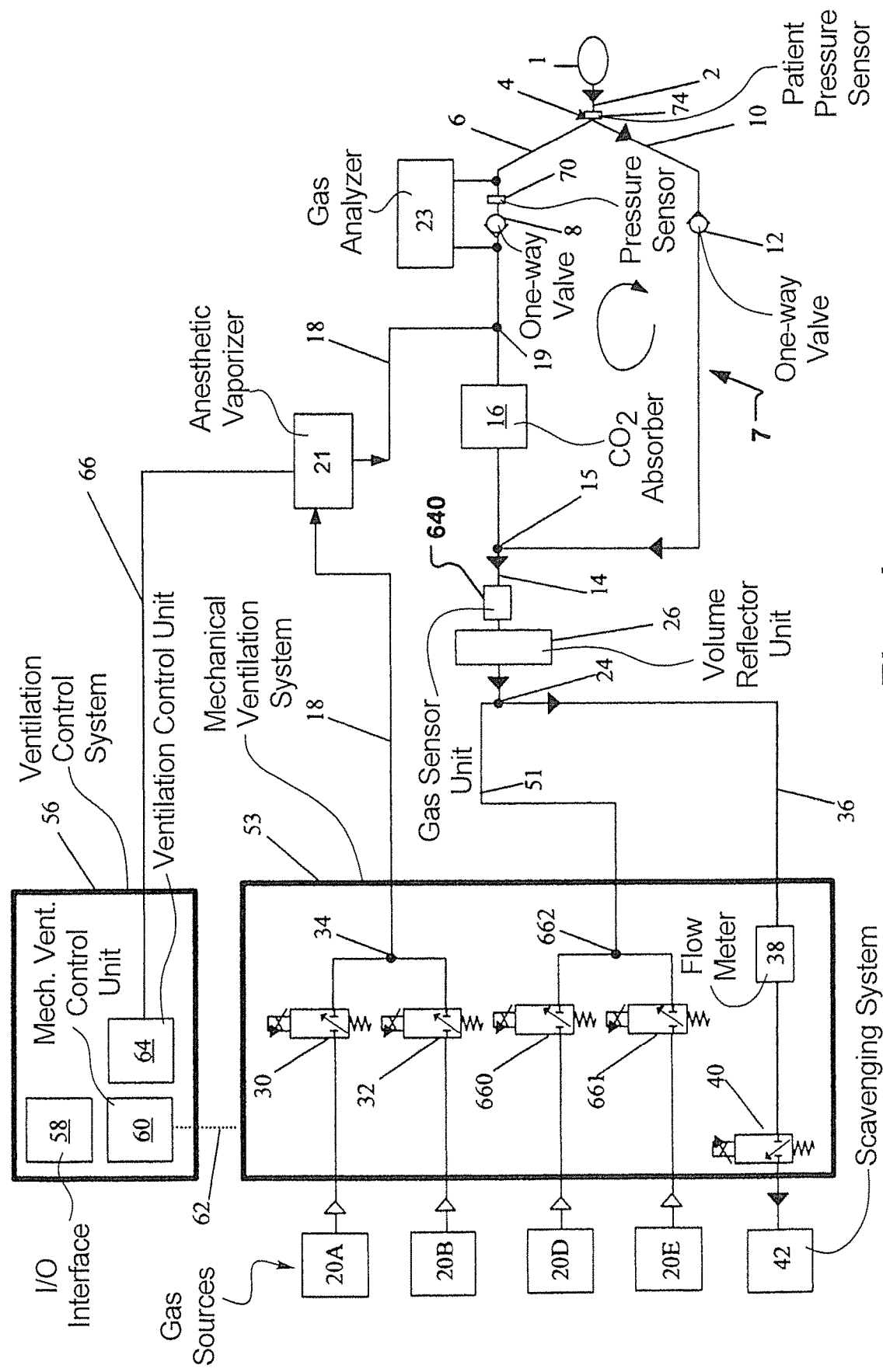
FIG. 1 is a schematic illustration of an anesthetic breathing apparatus having an anesthetic reflector unit, in an expiration phase in accordance with the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to a specific anesthetic breathing apparatus and arrangement of delivering reflector driving gas. However, it will be appreciated that the invention is not limited to this application but may be applied to many other anesthetic breathing apparatuses including for example multiplexed delivery of fresh gas supply and reflector driving gas, etc.

Figure 2:
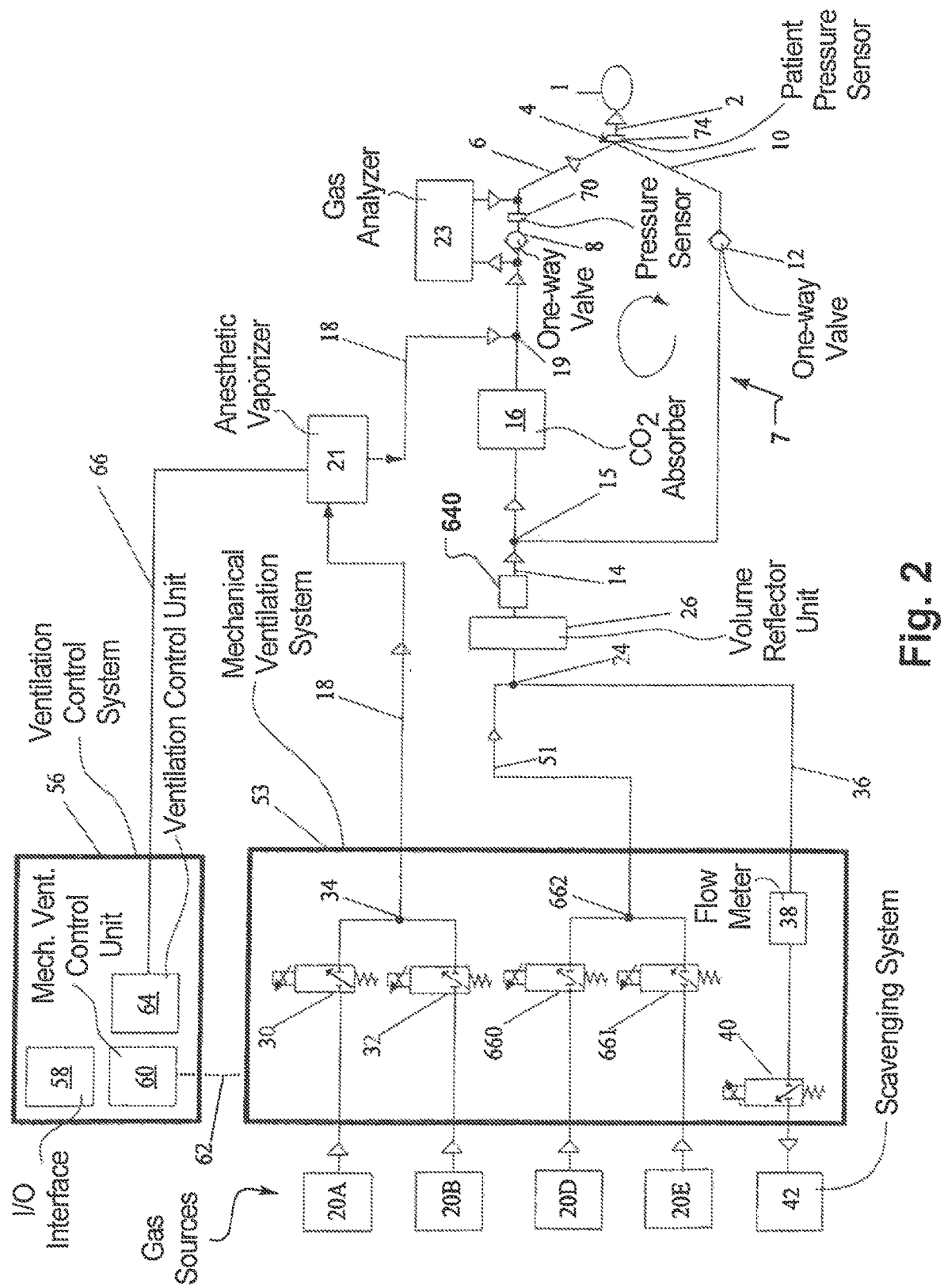
FIG. 2 is a schematic illustration of an anesthetic breathing apparatus having an anesthetic reflector unit, in an inspiration phase in accordance with the invention.
Figure 3:
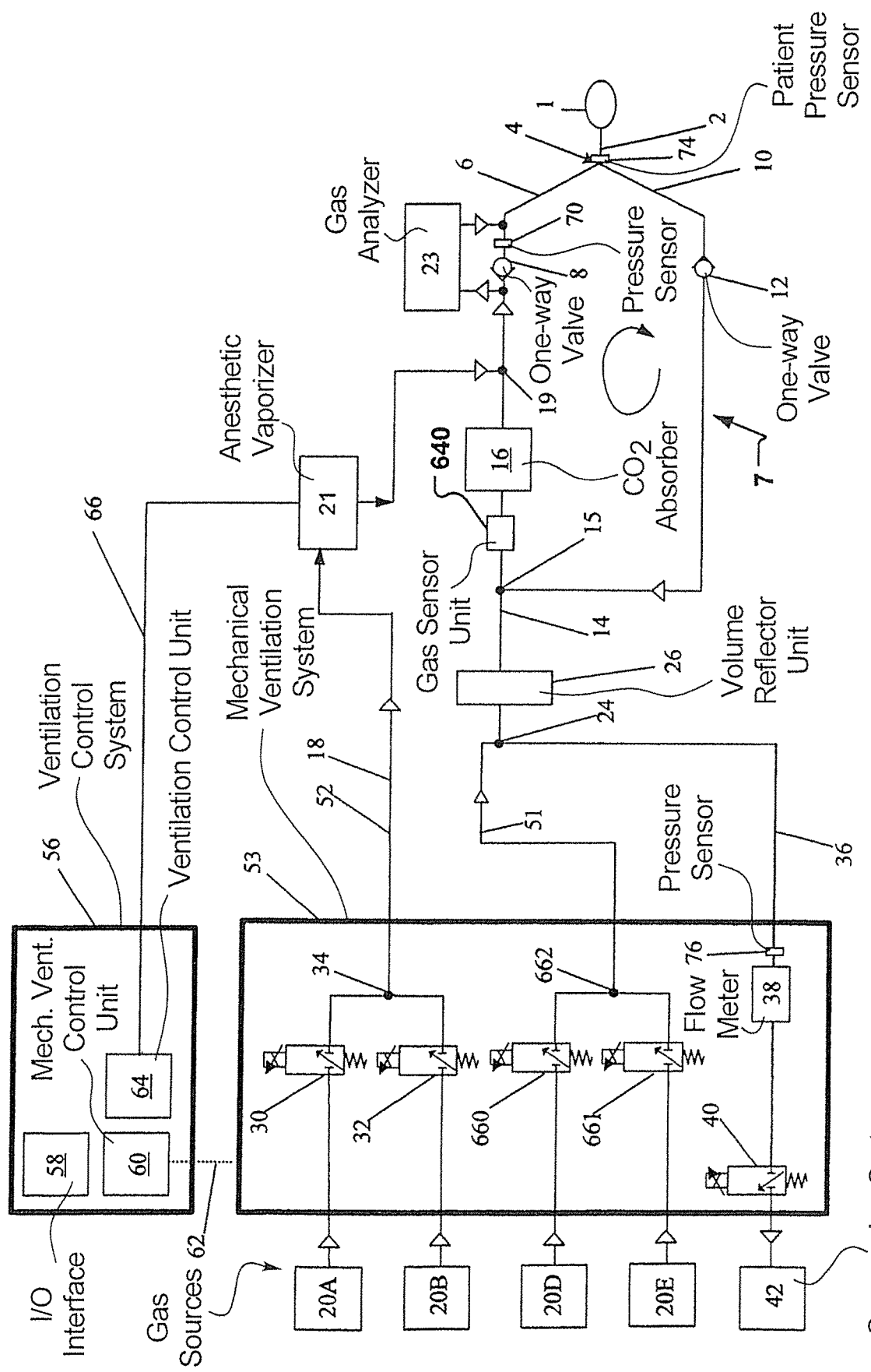
FIG. 3 is a schematic illustration of an anesthetic breathing apparatus having an anesthetic reflector unit, and a differently arranged sensor unit in accordance with the invention.

FIGS. 1 and 2 illustrates an embodiment of anesthetic breathing apparatus in which some embodiments of the control method may be implemented. An alternative embodiment is illustrated in FIG. 3 and described further below.

FIG. 1 shows schematically, a breathing circuit of an anesthetic breathing apparatus, coupled to a patient circle system 7 with a mechanical ventilation system 53.

The airways of a patient 1 are connected to a patient tube 2 of a Y-piece 4 in a circular tubing system with an inspiration tube 6 provided with a first one-way valve 8 and an expiration tube 10 provided with a second one-way expiratory valve 12. A patient pressure sensor 74 is provided in the patient tube 2 connected to the Y-piece 4. Downstream the second one-way valve 12, in FIG. 1 in a clockwise direction along the circle system 7, a common expiration and inspiration line 14 is provided for the delivery of inspiration gas to the patient and evacuation of expiration gas from the patient. The common expiration and inspiration line 14 is coupled to the circle system 7 at a junction 15. Further along the circle system 7, the tubing passes through a CO2 absorber 16.

Downstream the CO2 absorber 16 a fresh gas supply branch line 18 is provided to feed gas into the circle system 7 from a gas source. The fresh gas supply branch line 18 has a proximal portion in which fresh gas is supplied to an anesthetic vaporizer 21. The fresh gas is further conveyed via a distal portion of the fresh gas supply branch line 18, as desired enriched with gaseous anesthetic agent by the anesthetic vaporizer 21. The fresh gas supply branch line 18 is distally coupled to the circle system 7 at a junction 19.

The common expiration and inspiration line 14 is provided with a volume reflector unit 26.

When having a volume reflector, it may be designed in various ways. For instance, in order to provide a well-defined gas front, the channel or tube of the volume reflector is chosen to be narrow. However, this dimension is weighed against increased flow resistance. Also, compressible volume is chosen to be as low as possible. An adaptation of a volume reflector to different patient categories may be made by varying the channel and/or volume of the reflector. By providing a volume-variable volume reflector, undesired evacuation of exhalation gases may be avoided which otherwise may occur in case the volume reflector is too small compared to the tidal volume of the ventilated patient, while at the same time the responsiveness of the circle system may be maximized which otherwise may be poor in case the volume reflector is too big compared to the tidal volume. In specific embodiments, some portions of a volume-variable volume reflector may comprise a material that adsorbs anesthetic gases. When the exhalation gases passes through the volume reflector, the anesthetic agent is adsorbed by the adsorption material, and when the exhalation gas is pushed back to the patient by the reflector drive gas during the following inhalation, the anesthetic gases are desorbed and re-supplied to the patient. The additional adsorber ensures that the volume reflector may be made of smaller total volume, even if a volume of exhalation gas is evacuated from the circle system, nearly all anesthetic gas in the exhalation gas can still be re-supplied to the patient. This feature is effective when the volume reflector has a little bit too small compared to the tidal volume of the currently ventilated patient. Suitable means to vary the reflector volume are disclosed in patent application PCT/EP2007/062313, which published as WO 2009/062547 A1 and corresponding U.S. Patent Application Publication No. US 2010/0307490 A1, of the same applicant as the present application, which disclosures are hereby incorporated by reference in their entirety by reference for all purposes.

For example, the volume reflector unit 26 (FIGS. 1, 2, 3) may be embodied as an external part connected to patient cassette 306 (FIG. 6), such as comprises a first inlet 308 arranged to be connected to a drive circuit (e.g., see drive circuits of FIG. 1, 2 or 3), and two second inlets 314a-b arranged to be connected to an inhalation and exhalation branch, respectively, of a Y-shaped patient connector (not shown). The patient circuit of the patient cassette 306 may be incorporated within a housing 305 of a patient circuit module 302. In this embodiment, the patient cassette 306 comprises an outlet 318 which is pneumatically connected to the inlet 308 at a first branch point 322. The first branch point 322 is connected to a second branch point 324 via a common line which comprises a first 326 and a second 328, 330, 332 common-line portion. A common line should herein be construed as a gas conducting passage intended to convey gas in both directions, i.e. a gas line conducting a bidirectional gas flow. The second common-line portion 328, 330, 332 comprises a gas container 330 which is detachably connected external to the patient cassette housing 305 between a third 333 and a forth 334 inlet of the patient cassette 306. Two two-way valves 335, 336 are arranged in the common line, close to the first 322 and the second 324 branch points, for directing the gas flow within the common line through either the first 326 or the second 328, 330, 332 common-line portion. At the second branch point 324, the common line is branched into an inspiratory leg 338 and an expiratory leg 340. The inspiratory leg 338 is connected to the outlet 314a which is arranged to be connected to the inspiratory branch of a Y-shaped patient connector, and the expiratory leg 340 is connected to the inlet 314b which is arranged to be connected to the expiratory branch of the same Y-shaped patient connector. The patient cassette 306 further comprises a carbon dioxide (CO2) absorber 342, such as a soda lime canister, arranged to remove CO2 from the gas passing through the inspiratory leg 338, and a fresh gas inlet 344 which is pneumatically connected to the inspiratory leg 338 via a fresh gas supply line 348 for delivering additional fresh gas, typically oxygen, nitrous, oxide and anaesthetic, to the gas flow passing there through.

The function of the patient cassette 306 is described as follows when used in a circle system driven by a ventilator providing a controlled flow of drive gas, which acts directly on the exhalation gases from the patient, i.e. a volume reflector system. When the patient exhales, exhalation gases will enter the patient cassette 306 via the inlet 314b to which they are conveyed via the exhalation branch of the patient connector. The exhalation gases are conveyed through the expiratory leg 340 and into the second common line portion 332, 330, 328 to which they are directed by the two-way valve 336. To initiate inhalation, the ventilator delivers a flow of drive gas which enters the patient cassette via the inlet 308. The two-way valve 335 directs the drive gas flow into the second common line portion 328, 330, 332 in which a well-defined front between the drive gas and the exhalation gases is formed. The drive gas "pushes" the exhalation gases back through the second common line portion 328, 330, 332, into the inspiratory leg 338 and out through the inlet 314a from which it is conveyed to the patient via the inhalation leg of the patient connector. Before the exhalation gases are re-supplied to the patient, CO2 may be removed by means of the CO2 absorber 342 and additional fresh gas is added to the gas flow via the fresh gas supply line 348 in the inspiratory leg 338.

The outlet 318 is typically connected to the expiratory portion of the ventilator and during the exhalation phase, the drive gas that is pushed out of the second common-line portion 328, 330, 332 by the exhalation gases is directed into the expiratory portion of the ventilator through the outlet 318. Often, an expiratory valve in the expiratory portion of the ventilator may be configured to open at a predetermined pressure against which the patient exhales, thus constituting what is known in the art as a positive end expiratory pressure (PEEP) valve. The patient cassette 306 may comprise a valve arrangement 350 arranged between the first branch point 322 and the outlet 318, which valve arrangement 350 can comprise such a controllable PEEP valve. This is advantageous in case the outlet 318 is not connected to an expiratory portion of a ventilator but directly connected to atmosphere, a scavenging system for isolating the discharged gas, or to a recovery system for recovering at least some of the gas components in the discharged gas. In that way, a PEEP can always be applied to the patient connected to the circle system.

The second common-line portion 328, 330, 332 thus serves as a volume reflector in which a well-defined front between the drive gas and the exhalation gases is pushed back and forth. If the volume of the volume reflector 328, 330, 332 is smaller than the tidal volume of the ventilated patient, not only the drive gas but also some of the exhalation gases following the drive gas will leave the circle system through outlet 318 during exhalation, causing an undesired loss of, e.g., expensive anaesthetic gases that one would like to re-supply to the patient during the following inhalation and a demand for higher fresh gas flow through the fresh gas supply line 348 to compensate for the evacuated exhalation gases. If, on the other hand, the volume of the volume reflector 328, 330, 332 is much bigger than the tidal volume of the ventilated patient, the compressible volume in the patient circuit is increased, causing decreased responsiveness of the circle system and decreased accuracy in the control thereof. Since the patient cassette 306 comprises a third and a forth inlet 333 and 334 between which different gas containers having different volumes can be detachably connected to form a volume-variable portion 330 of the volume reflector 328, 330, 332, the volume reflector can be tailored so as to always suit the tidal volume of the currently ventilated patient. Preferably, the volume-variable portion 330 is chosen so that the total volume of the volume reflector 328, 330, 332 is equal to, or slightly bigger, than the tidal volume of the patient. The tidal volume of a patient can be roughly calculated as 6-7 ml per kilogram bodyweight. That is, the tidal volume and hence the recommended minimum volume of the volume reflector 328, 330, 332 may be approximately 0.1 litre for a paediatric patient weighing 15 kilos and 0.7 litres for a fully grown man weighing 100 kilos. It should be pointed out that the volume of a typical patient circuit (any volume reflector excluded) may be approximately 0.2 litres.

Figure 6:
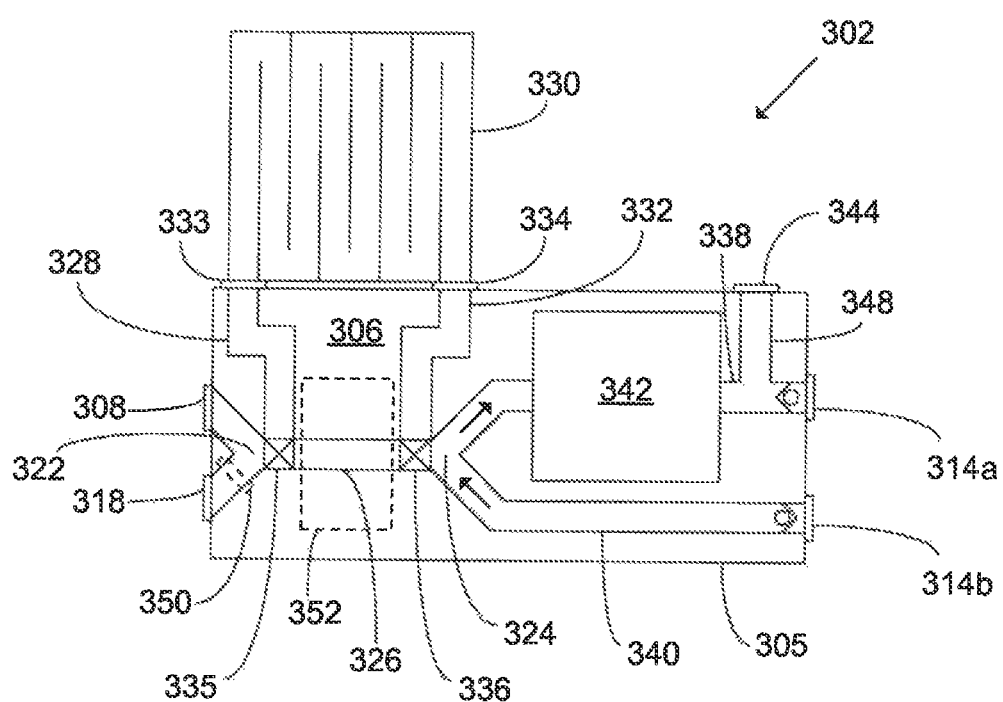
FIG. 6 is a schematic illustration of a non-limiting patient cassette embodiment with variable patient circuit volume.

It should be noted that the inlet 308 also may be connected to a common line of the ventilator, which common line is branched into an inspiratory portion and an expiratory portion of the ventilator, respectively, outside the patient cassette 306. In such a case, the point of the breathing circuit corresponding to the first branch point 322 in FIG. 6 is situated external to the patient cassette 306. Since the volume reflector is the volume of the common line between the first branch point and the second branch point 324, this implies that some of the volume reflector is located outside of the patient cassette 306 and rather is to be regarded as a part of the drive circuit. Nevertheless, there is still a need to vary the volume of the volume-reflector portion comprised in the patient cassette 306 so as to adapt the total volume of the volume reflector to the tidal volume of the patient. In this case, the outlet 318 of the patient cassette 306 is redundant and can be held closed.

The gas container 330 in the illustrated embodiment of FIG. 6 depicts a plastic box comprising a folded gas conducting passage. It should be noted that the cross section area of the gas conducting passage in the gas container 330 should not be too big in order for the front between the drive gas and the exhalation gas to be well-defined.

Figure 7:
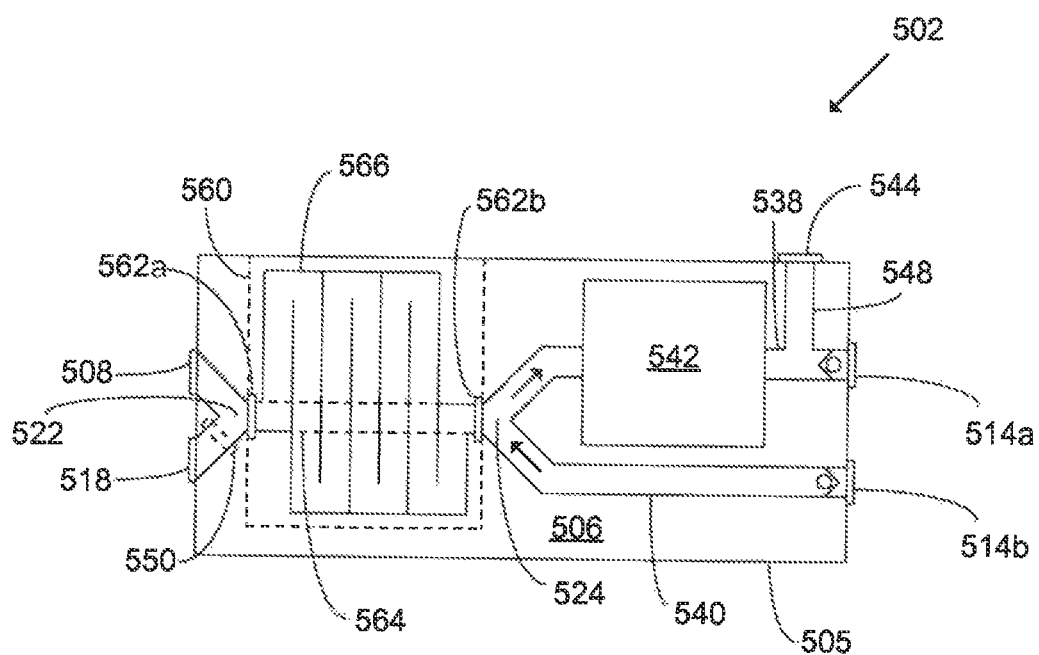
FIG. 7 is a schematic illustration of another non-limiting patient cassette embodiment with variable patient circuit volume.

FIG. 7 illustrates another embodiment of a patient cassette 506. In this embodiment, volume reflector unit 26 (FIGS. 1, 2, 3) may be embodied as part of patient cassette 506 (FIG. 7), the patient cassette housing 505 comprises a lid 560 which is openable to expose two connection means 562*a-b* in the interior of the patient cassette 506. The first 562*a* and second 562*b* connection means are arranged in the common line of the patient circuit and is pneumatically connected to the first branch point 522 and the second branch point 524, respectively. The connection means 562*a-b* allow different gas conduits 564, 566 with different volumes to be detachably connected there between to form a volume-variable portion of the common line of the patient circuit. By inter-connecting a gas conduit 564 with a small volume between the connection means 562*a-b*, the patient circuit volume is minimized to optimize the patient cassette 506 for use in an anaesthetic reflector system. By inter-connecting a gas conduit 566 with a larger volume between the connection means 562*a-b*, which volume is based on the tidal volume of the ventilated patient, a perfectly sized volume reflector is introduced, optimizing the patient cassette 506 for use in a volume reflector system.

By "hiding" the volume-variable portion of the patient circuit internal to the housing 505 of the patient cassette 506, the patient cassette can be made compact and easily movable. By providing the patient cassette with a lid 560 or by other means make sure that the connection means 562*a-b* are easily accessible, the volume of the patient circuit can be manually varied in a simple way.

However, even in these adaptive cases or volume reflectors with adsorber portions, reflector driving gas may pass the reflector into the circle system. Embodiments of the present invention facilitate to take control of such situations where re-breathing of anesthetic gases is maximized, but still driving gas passes the volume reflector during inspiration.

In embodiments the volume reflector 26 has a reflector volume that is fixed. The reflector volume may for instance be in the range of approximately one liter. This reflector volume is substantially less than previously applied reflector volumes, while a good performance is provided for a large variety of patient categories. A reflector volume of approximately one liter, is for instance in certain embodiments in a range between 1.3 liters to 0.7 liters, or 1.2 liters to 0.8 liters or 1.1 liters to 0.9 liters. The fixed reflector volume may be changed to other sizes of less volume for specific patient categories.

The fresh gas inhalation source may comprise multiple gas sources, such as an oxygen gas source 20A, and an air gas source 20B, as illustrated in FIG. 1. Additionally, the fresh inhalation gas source may comprise a nitrous oxide gas source (not shown).

The anesthetic vaporizer 21 is fluidly connected to the fresh gas supply branch line 18 downstream the multiple gas sources and upstream the junction 19. Multiple anesthetic vaporizers may be provided. The anesthetic vaporizer 21 is devised to vaporize a volatile anesthetic agent into the fresh gas flow that is delivered into the circle system 7 and with a flow of inspiratory gas to the patient 1. In an exemplifying breathing circuit the vaporizer 21 be an injection type vaporizer.

A gas analyzer 23 is provided to analyze gas contents with an input of sample inspiratory gas in a sidestream configuration. The sidestream is tapped downstream the junction 19 and upstream the first one-way valve 8 in the inspiratory branch. After analysis in gas analyzer 23, the sample gas is recirculated to the inspiratory flow downstream the first one-way valve 8 and upstream the Y-piece 4 in the inspiratory branch. A pressure sensor 70 is provided between the first one-way valve 8 and the recirculation point of the sample gas.

At the side turned opposite the circle system 7, the volume reflector 26 of the common expiration and inspiration line 14 is coupled at a junction 24 to a reflector driving gas line 51 for pushing reflector driving gas into the proximal end of the volume reflector. Thus gas may be pushed out of the distal end of the volume reflector into the common expiration and inspiration line 14 downstream the volume reflector 26 and into the circle system 7.

During inhalation, a gas flow ratio may thus be controlled between the fresh gas line 18 and the line 14 in order to adjust a degree of re-breathing gas being pushed from volume reflector 26 via line 14 into the breathing circuit 7.

Oxygen gas source 20A is coupled to an O2 inspiratory valve 30 that in its turn is connected to the fresh gas line 18 at a blender 34. Similarly, air gas source 20B is coupled to an air inspiratory valve 32 that also is coupled to the fresh gas line 18 at the blender 34. The O2 inspiratory valve 30 and the air inspiratory valve 32 are devised for adjusting the inlet flow and the proportions of the respective gases into the fresh gas line 18 prior to adding anesthetic agent in vaporizer 21. Only O2 and air are shown, but nitrous oxide may also be used from a nitrous oxide gas source a nitrous oxide inspiratory valve (not shown), which alternatively replace the air gas source 20B and air inspiratory valve 32.

A ventilation control system 56 may comprise a user input/output interface 58 with command input means and display means of a per se known type.

Also, the ventilation control system 56 may comprise mechanical ventilation control unit 60 usually comprising specifically designed computer program code for controlling the operation of the mechanical ventilation system 53 and its components via a symbolically shown control line 62. The mechanical ventilation control unit 60 enables vent of breathing gas from the mechanical ventilation system according to a set of predetermined control rules for controlling the expiratory valve 40 in accordance with ventilation mode requirements. In effect, the expiratory valve may in this connection be controlled to open or close at pre-defined pressure levels that occur in the tubing system. For instance, the control rules implement a mechanical ventilation mode comprising pressure control functions of the patient pressure. During expiration, a positive end expiratory pressure (PEEP) may be adjusted by the expiratory valve 40 at the end of the expiratory breathing phase, before the next inspiration phase starts. The expiratory valve 40 may also be operated to implement an adjustable pressure limit function during a manual ventilation mode. The expiratory valve 40 is usually closed during inspiration and controls the expiratory pressure level, and expiratory flow, during expiration.

The control unit 60 is adapted to detect a reflector driving gas (RDG) crossing over the volume reflector unit 26 during inspiration based on the at least one property of the gas stream measured by a gas sensor unit 640. The control unit 60 is further is adapted to set operational modes of said apparatus. Thus the control unit 60 provides for controlled admixture of reflector driving gas (RDG) into the patient circle system 7.

The ventilation control system 56 further comprises an anesthetic agent control unit 64. The anesthetic agent control unit 64 is devised to control the anesthetic vaporizer 21 via the symbolically shown control line 66.

An evacuation line 36 is connected to the common expiration and inspiration line 14 and to the reflector driving gas line 51 at the junction 24. The evacuation line 36 leads (via a flow meter 38 as shown in the embodiment of FIG. 3) and a pressure sensor 76 to an expiratory valve 40 that is devised to control output of evacuated gas flow from the circle system 7 to a scavenging system 42 or to the atmosphere.

A measure for gas flow via fresh gas supply branch line 18 is provided by suitable gas flow sensors. For instance oxygen gas sources 20A, 20D and/or air gas sources 20B, 20E may have integrated flow meters. Alternatively, or in addition, O2 inspiratory valve 30, air inspiratory valve 32, and/or valves 660, 661 may have integrated flow meters, providing units known as "gas modules". Alternatively, a separate gas flow sensor may be provided in fresh gas supply branch line 18, or in vaporizer 21.

The mechanical ventilation system 53 comprises in this embodiment one or more additional inspiratory valves 660, 661, also called gas modules. The inspiratory valves may be highly sophisticated sub-systems of the anesthetic breathing apparatus, having an inherent high precision gas flow and pressure control.

The breathing apparatus comprises in addition to the fresh gas inhalation source further gas sources, such as an oxygen gas source 20D, and an air gas source 20E, as illustrated in FIG. 1. The further gas source provides a reflector driving gas (RDG).

Alternatively, or in addition, the oxygen gas source 20A may be coupled to the input of inspiratory valve 660, and the air gas source 20B may be coupled to the input of the inspiratory valve 661. In this case, the gas sources 20D, 20E may be omitted and the inspiratory valves 30, 660, and 32, 661, may be driven from single gas sources respectively. The multiple inspiratory valves 30, 32, 660, 661 are called "multi-packs" of valves, in the present example a "four-pack" of inspiratory valves.

The inspiratory valves 660, 661 are controlled to provide a desired oxygen concentration at a junction or blender 662. Only O2 and air are shown, but nitrous oxide may also be used. Alternatively only one of inspiratory valves 660, 661 is implemented in a "three-pack" of inspiratory valves.

Gas flow from inspiratory valves 660, 661 via blender 662 is provided to the reflector driving gas line 51. Gas flow from inspiratory valves 30, 32 via blender 34 is provided to the fresh gas line 18.

A ratio of total flow between the reflector driving gas line 51 and the fresh gas line 18 is adjustable by suitably controlling a portion of gas flow via blender 34 and blender 662 respectively. In this manner, the distribution of the amounts of gas flow between the reflector driving gas line 51 and the fresh gas line 18 is adjustable in real time.

The flow delivered to the patient during inspiration is thus defined by the sum of gas provided by the reflector driving gas line 51 and the fresh gas line 18.

Thus, the "multi-pack" of inspiratory valves may be actuated to a variety of flow selection modes where an amount of gas is enabled to flow to the patient via the common expiration and inspiration line 14, and/or via the supply branch line 18, as fresh gas, then bypassing the CO2 absorber 16. An arbitrary ratio may be adjusted between the reflector driving gas line 51 and the fresh gas line 18 by controlling the inspiratory valves 30, 32, 660, 661 in desired manner. Thus, a desired re-breathing fraction (RBF) is adjustable by controlling the "multi-pack" of inspiratory valves.

The distribution of the amounts of gas flow between the fresh gas line 18 and the reflector driving gas line 51 is adjustable in real time by control unit 60.

Thus, the control unit 60 may actuate various flow selection modes where an amount of gas is enabled to flow to the patient via the common expiration and inspiration line 14, and/or via the fresh gas line 18, as fresh gas, then bypassing the CO2 absorber 16. An arbitrary ratio may be adjusted between the fresh gas line 18 and the reflector driving gas line 51.

For instance by distributing the entire flow of gas from junction 34 to the fresh gas line 18, the re-breathing fraction (RBF) is zero, i.e. the entire flow of inspiratory gas into patient 1 originates from this line 18, including an addition of one or more anesthetic agents from vaporizer 21.

In order to increase the RBF, a portion of the flow of gas from junction 34 is instead provided via line 14, provided from pushing gas from volume reflector 26 into the breathing circuit, by suitably controlling the gas flow in reflector driving gas line 51. The gas pushed out of the volume reflector 26 is blended with gas originating from the fresh gas line 18 at junction 19 and further conveyed into the patient 1. The gas pushed from the volume reflector and/or adsorption filter 26 into the breathing circuit 7 is composed of previously exhaled patient gas, e.g. including one or more anesthetic agents. Hence, this previously exhaled patient gas is provided for re-breathing to the patient, after passing through the CO2 absorber 16. In a low flow operational mode (i.e. the highest possible RBF), the breathing apparatus may be controlled in such a manner that only the anesthetic agent and oxygen consumed by the patient is re-added to the circle system 7. In case too little oxygen is admixed to the circle system 7, the patient may subject to hypoxia, which is undesired.

Further, the anesthetic breathing apparatus comprises gas sensor unit 640. As can be seen in FIGS. 1, 2 and 3, the sensor unit is fluidly connected and arranged upstream the junction 19 where the fresh gas supply branch line 18 joins the circle system 7. In the embodiment in FIGS. 1 and 2, the sensor unit is arranged upstream the carbon dioxide absorber unit 16 and downstream the reflector unit 26 in the common line 14. The sensor unit may alternatively be positioned downstream the junction 15 where the reflector joins the circle system 7.

The terms upstream and downstream used herein are as seen during an operational inspiration phase of the breathing apparatus, as shown in FIG. 2.

The sensor unit 640 is a gas identification unit, a gas concentration measurement unit, and/or a gas flow measurement unit, as will be described in more detail below.

A volume reflector is, amongst others, a storing element for one or more anesthetic agents, from which the latter are intermittently returned to the breathing circle, like a bag in bottle system, but without a separating membrane between the driving gas side and the patient connection side at the breathing circle. Thus, an anesthetic agent present in the breathing circle is retained in the breathing circle until it is eventually washed out. However, as will be described in more detail below, reflector driving gas may cross the volume reflector and enter the circle system 7.

The sensor unit 640 is devised to provide a measurement for detecting that reflector driving gas has passed all the way from the reflector driving gas line through the volume reflector unit 26 and has reached the sensor unit. Thus, it is detectable that reflector driving gas has entered, or is about to enter the circle system 7. That means that all previously exhaled gas, stored in the volume reflector has been pushed out of the volume reflector and that a break-through of reflector driving gas across the volume reflector is present.

Control of fresh-gas flow and composition may be based on having a gas analyzer 23 arranged to measure gas concentrations in the circle system 7 downstream the fresh gas junction 19. However, feedback control of fresh gas composition only based on measurements from gas analyzer 23 cannot be stable when a gas component, other than fresh gas, such as reflector driving gas passing the volume reflector 26 into the circle system 7 at junction 15, enters the circle system 7 upstream the gas analyzer 23 and affects the gas composition outside of the feedback control loop. The feedback control may thus eventually become unstable, such that reliable delivery of e.g. anesthetic agent concentration to the patient 1 becomes difficult.

Hitherto there has been no need to provide gas measurements upstream fresh gas supply junction 19, as passing of reflector driving gas over the volume reflector 26 has been avoided by all means. Moreover, as gas analyzers are rather expensive equipment, there was no incentive to add further gas analyzers to anesthetic breathing apparatuses upstream junction 19.

Therefore, in embodiments, a gas sensor unit 640 is arranged to measure at least one property of the gas stream upstream the fresh gas connection 19 and downstream the reflector unit 26 and is adapted to provide a signal allowing detection of a reflector driving gas (RDG) crossing over the volume reflector 26 during inspiration based on the at least one property of the gas stream measured by the gas sensor unit 640.

The gas sensor unit 640 is a unit that is arranged to measure at least one property of the gas stream upstream the fresh gas connection 19 and downstream the reflector unit 26. The property of the gas stream is directly or indirectly related to the composition of the gas. The gas sensor unit 640 may be devised to analyze the gas composition present between the volume reflector 26 and the inspiratory limb, as illustrated by inspiration tube 6.

The gas sensor unit 640 may be based on measuring one or more of the following physical properties of the gas: heat conductivity, light absorption, paramagnetic properties, sound propagation speed in the gas, density of the gas, Doppler shift of a sound wave in the gas, molecular weight of the gas, etc. In some embodiments, also a flow of the gas is such a property of the gas. In some embodiments, such a property of the gas is gas flow related properties of the gas, such as displaced volume. From gas flow, other entities may be calculated, such as flow rate, or gas volume displaced during a gas flow time period.

In embodiments, the gas sensor unit is a gas sensor capable of measuring absolute or relative concentration of at least one specific gas component.

In some embodiments, the gas sensor unit 640 is alternatively, or in addition, devised to measure the property of gas flow at a measurement position thereof. Gas flow measurement may be provided unidirectional or dependent on direction of the gas flow out of the volume reflector and/or into the volume reflector. The gas flow sensor may be based on various physical principles, including the aforementioned or e.g. differential pressure drop measurement over a defined distance in a gas line at said measurement point.

In an embodiment the gas flow sensor is based on an ultrasonic working principle. Here, time of flight measurements provide a signal for gas flow measurements. In addition, measured ultrasonic sound propagation speed (at zero flow, e.g. at the end of expiration), provides a measure for gas concentration or gas presence measurements, but at least for detecting changes of gas concentrations. A gas senor unit 640 based on ultrasonic measurements, may also be devised to measure the molecular weight of gases measured by measuring the ultrasonic sound propagation speed. As for instance anesthetic agents, such as halogenated fluorocarbons, have a much higher molecular weight than RDG, the presence or absence of such anesthetic agents is particularly well detectable by an ultrasonic gas sensor.

Conventional anesthetic breathing apparatuses comprise a separate expiratory flow meter 38, as illustrated in FIG. 3. In some embodiments the gas sensor unit 640 replaces such dedicated separate expiratory flow meter 38. When arranged in common line 14, as shown in FIGS. 1 and 2, the gas sensor unit 640, e.g. in form of an ultrasonic flow meter, is positioned downstream (as defined during inspiration) of the volume reflector 26 in the expiration and inspiration line 14, an anesthetic breathing apparatus is provided that has added functionality and safety without increasing cost of the apparatus.

The gas flow during the expiratory phase is illustrated by the bold arrows on gas flow lines in FIG. 1. During expiration, the expiratory valve 40 is controlled to release gas to the evacuation 42. Exhalation gas from the patient 1 passes through the expiratory part of the circle system 7 and via junction 15 into the line 14 and volume reflector 26. The expiratory flow is measured by the gas flow meter (gas sensor unit 640) in line 14. Expiratory gas enriched with exhaled anesthetic agent is pushed into the volume reflector 26. The reflector driving gas from the previous inhalation present in the volume reflector is pushed towards the expiratory valve 40 and further to evacuation 42. Expiratory pressure, e.g. for a positive end expiratory pressure (PEEP) regulation is provided by pressure sensor 76. A separate expiratory flow meter is not necessary and would only provide redundant information. Gas sensor unit 640 provides the expiratory flow information.

Returning to FIG. 2, is shown that, during inspiration, the same gas flow sensor (gas sensor unit 640) measures the gas flow leaving the volume reflector 26 via line 14 to the circle system 7. The gas flow during the inspiratory phase is illustrated by the bold arrows on the gas flow lines in FIG. 2. By providing the gas flow sensor unit 640 downstream the volume reflector 26 and upstream the fresh gas junction, information concerning the gas flow and/or gas composition entering the circle system via line 14 at junction 15 is provided.

Alternatively, or in addition, gas flow through the volume reflector may be provided from a flow sensor in the gas source for the reflector driving gas. The gas modules 30, 32, 660, 661 may have integrated gas flow sensors. A gas flow measure provided from the gas source for the reflector driving gas is a measure for gas flow through the volume reflector 26. In this case it is sufficient that the gas sensor unit 640 only detects certain type of gas, measures absolute concentration of certain gas, or detects relative changes of a concentration of a certain gas, without being capable of measuring gas flow.

In practice very often a portion of the exhaled gas is lost by leakage, e.g. passing a cuff of patient tube 2 intubated into the trachea of the patient 1. Such leakage volume has to be compensated for during the next inspiration phase. Hence, the volume reflector is not filled with the entire exhaled volume (leakage volume is lost).

This provides a basis for actually measuring the leakage volume in the anesthetic breathing apparatus.

In case no fresh gas is supplied via fresh gas line 18 to the circle system 7 at junction 19, all inspiration volume is provided via the volume reflector 26 and common line 14 to junction 15, and further to the patient via carbon dioxide absorber 16. Leakage volume is calculated as (inspiration volume provided during the present inhalation phase minus expiration volume measured entering the volume reflector during the previous exhalation phase). Hence, a leakage volume is based on a difference of an inspiratory gas volume measured by said gas senor unit 640 comprising a volume leaving said reflector unit 26 during inspiration and a volume entering said reflector unit 26 during the preceding expiration. The entire inspiratory gas volume may also comprise a known portion delivered via the fresh gas line 18.

In case a certain portion of the inspiration volume is provided via the fresh gas line 18, this volume is known from gas modules 30, 32, when these have integrated flow sensors. The entire inspiration volume is known when integrated flow sensors are provided in gas modules 660, 661. As leakage might occur, e.g. in the volume reflector and/or connected gas lines, the gas sensor unit 640 may provide a leakage detection during inspiration or plausibility check information.

However, as the provided inspiration volume is larger than the (measured) exhalation volume, enriched with anesthetic agent, reflector driving gas will be pushed out of the volume reflector 26 into the patient circuit 7.

When the previous exhalation volume has been pushed out of the volume reflector 26, reflector driving gas will be detected by gas sensor unit 640.

The amount of reflector driving gas is calculated from the flow, and the gas type thereof, entering the circle system 7 is thus known.

Alternatively, or in addition, reflector driving gas passing the volume reflector 26 may be detected when reflector driving gas volume provided during inspiration exceeds the previous expiratory volume entering the volume reflector 26.

Once reflector driving gas is detected by gas senor unit 640 during inspiration, appropriate action can now be taken by control unit 60 to ensure that the patient receives a desired amount and composition of inspiratory gas.

For instance, when the reflector driving gas is oxygen, supplied by oxygen source 20D, the admixture of fresh gas is adjusted accordingly in order to provide for a constant anesthetic agent concentration provided to the patient 1. As the dilution factor of added reflector driving gas upstream the fresh gas delivery junction 19 is known, the amount of anesthetic agent is increased accordingly to compensate for this dilution factor. The feedback control loop based on measurement from anesthetic gas monitor is thus improved based on compensation for said dilution factor.

In addition, the delivery of sufficient oxygen provided in the inspiratory gas delivered to the patient and hypoxia is effectively avoided.

In case gas sensor unit 640 is only capable of detecting relative changes of a concentration of a certain gas, a system having particular low manufacturing cost may be provided. By means of such a gas sensor unit adapted to detect relative gas composition changes, a change of gas composition is detectable during the inspiratory phase, such as towards the end of the inspiratory phase. This change of gas composition is caused by the trailing reflector driving gas pillar having a different composition than the leading gas from the previous exhalation, comprising a completely different composition with regard to gaseous components including carbon dioxide (not present in RDG), anesthetic agent (not present in RDG) and oxygen (higher concentration in RDG). A detected change in carbon dioxide presence, or an absence of carbon dioxide, may be used as a measure for RDG crossing the volume reflector 26.

Appropriate actions upon RDG entering the circle system 7 may then be taken, as explained herein. For instance, the re-breathing fraction (RBF) may be reduced, or the concentration of anesthetic agent in the fresh gas may be appropriately increased. This action may be provided with a suitably calculated time delay, such that the time of travel of the RDG in the circle system and the time of travel of the fresh gas from the vaporizer is considered for a real time adjustment of inhalation gas admixture at junction 19.

RDG flow may be adjusted such that a front of a RDG column reaches said gas sensor unit 640 at an end of said inspiratory phase. The sensor signal provided by said gas sensor unit 640 provides a suitable feedback to the control unit 60 for this purpose.

Delivery of RDG may be stopped upon detection of the reflector driving gas (RDG) crossing over said volume reflector 26.

In case the RDG is air, such as provided by air gas source 20E, it may be desired to avoid that the RDG flows into the patient circuit and towards inspiration by the patient 1. One reason is that air only comprises approx. 21% oxygen and hypoxia is more likely when air enters the circle system 7. In this case, when RDG (air) is detected by the gas sensor unit 640, further delivery of RDG may be stopped, an inspiration gas is delivered to circle system only from fresh gas supply line 18 at junction 19. The fresh gas is chosen to have a suitably high concentration of oxygen. Hypoxia is thus effectively avoided by providing sufficient oxygen to the patient.

In addition, a plausibility check of system function may be provided. When measuring gas concentration with a gas sensor unit, gas concentration of RDG may be measured. In this case the system is within specification, when the identified gas type after the detected relative change of gas concentration (dip or peak) corresponds to the actual RDG used.

Alternatively, or in addition, the user of the anesthetic breathing apparatus may be provided with a warning or indication that RDG is passing the reflector volume. Alternatively, or in addition, the user may be presented related information, such as leakage volume. Based on this information, the user may make appropriate adjustments of e.g. mechanical ventilation parameters, or check intubation cuffing, etc.

A further embodiment of the invention is illustrated in FIG. 3. The anesthetic breathing apparatus has sensor unit 640 arranged downstream junction 15. In this embodiment, the gas sensor unit 640 measures flow or concentration related to RDG detection only during inspiration. This is sufficient to detect RDG passing the volume reflector 26 and entering the breathing circuit 7. The additional expiratory flow meter 38 measures expiratory flow, and may be used to detect leakage flow.

Figure 8:
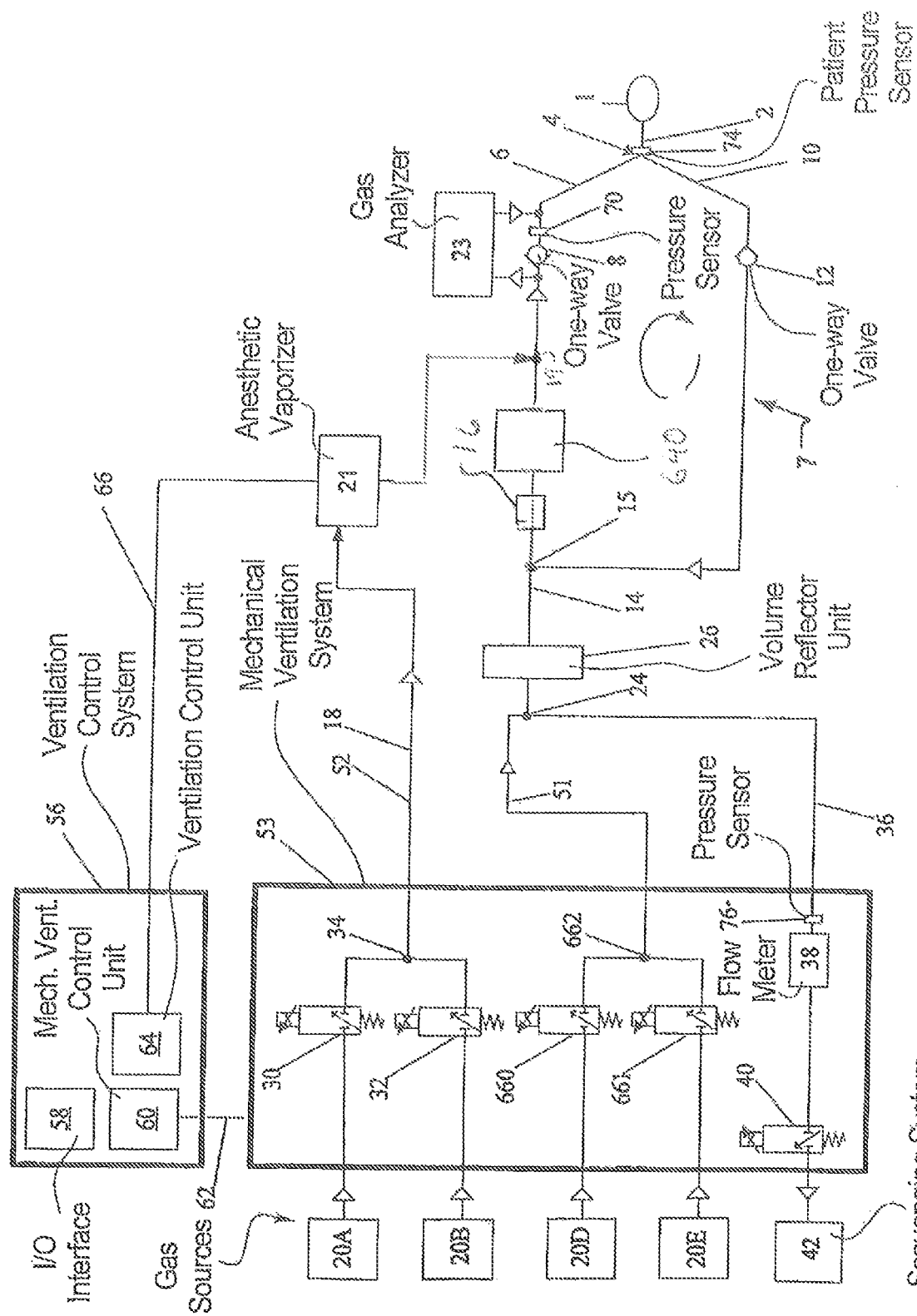
FIG. 8 is a schematic illustration of an anesthetic breathing apparatus having an anesthetic reflector unit, and a differently arranged sensor unit in accordance with the invention.

In alternative embodiments to FIG. 3 (as reflected by FIG. 8 for example), the anesthetic breathing apparatus has a sensor unit 640 arranged downstream junction 15 and downstream the carbon dioxide absorber 16, but upstream fresh gas junction 19. This arrangement may have undesired delays in detecting RDG crossing the volume reflector as RDG has already entered the circle system 7. However, upon detection of RDG, appropriate action may also be taken as in the embodiment described above, with reference to FIG. 3.

In embodiments, RDG crossing a volume reflector into a circuit system 7 is no longer undesired, except in embodiments where air is used as RDG. Thanks to the embodiments, the RDG entering the circuit system 7 is advantageously controlled and handled. Safety of the anesthetic breathing apparatus is thus considerably increased while not increasing cost and allowing for advantageous ventilation of a patient 1. Inspiratory ventilation of the patient with sufficient anesthetic agent, as desired by the user, is ensured in real time. Advanced mechanical ventilation forms may be used in an anesthetic breathing apparatus. Reflector volume may be limited to a necessary volume. Thus, the anesthetic breathing apparatus may be provided in a compact form.

Manual ventilation with RDG may be provided by suitably adding a manual ventilation bag to the anesthetic breathing apparatus, e.g. in the evacuation line 36. The breathing apparatus offers thus both a manual and an automatic ventilation mode. The user may choose between manual or automatic ventilation by turning a control knob or the like on the breathing apparatus.

Figure 4:
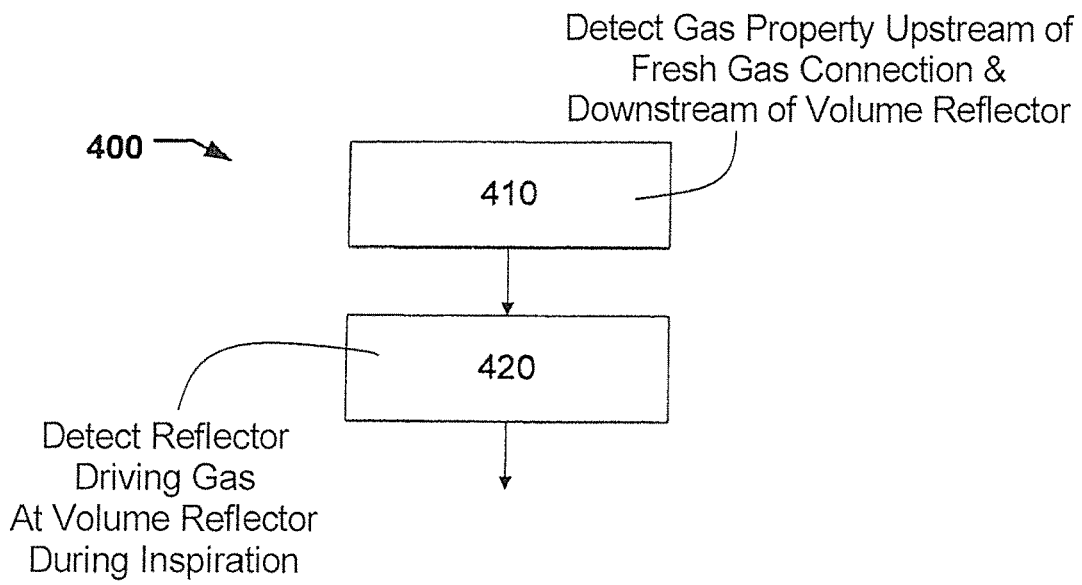
FIG. 4 is a flow chart of a method in accordance with the invention.

FIG. 4 is a flow chart of a method 400. The method is a method 400 of detecting a reflector driving gas (RDG) crossing over a volume reflector 26 into a circle system 7 in an anesthetic breathing apparatus, such as described above. The method comprises measuring 410 at least one property of a gas stream upstream a fresh gas connection 19 and downstream a reflector unit 26 by means of a gas sensor unit 640, and detecting 420 said reflector driving gas (RDG) crossing over said volume reflector 26 during an inspiration phase, based on said at least one property of said gas stream measured by said gas sensor unit 640.

Figure 5:
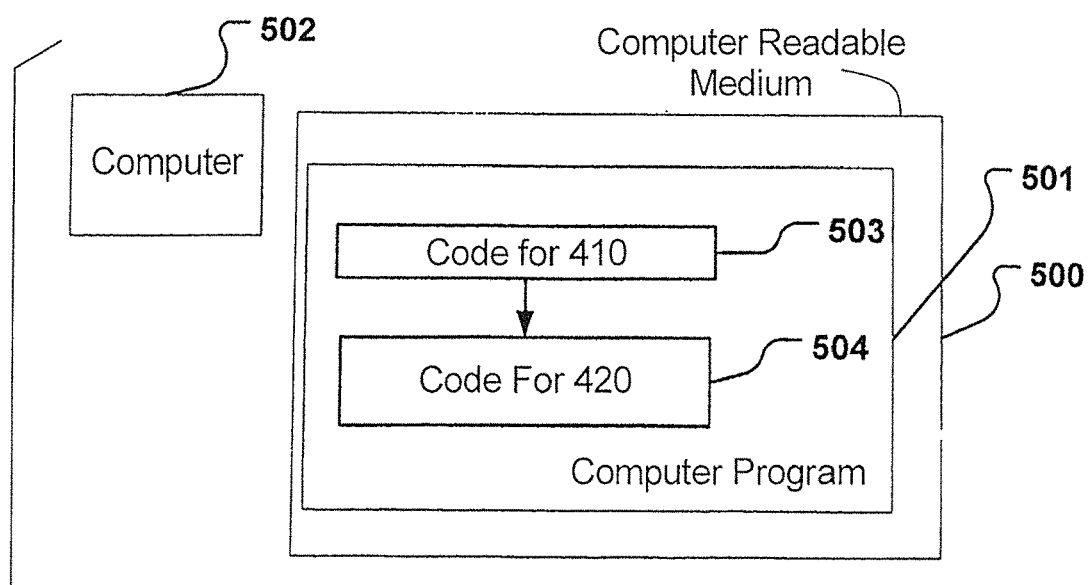
FIG. 5 is a schematic illustration of the organization of programming instructions for storage on a computer-readable medium in accordance with the invention.

FIG. 5 is a schematic illustration of a computer program 501 representing programming instructions (control commands) in a form suitable for storage on a computer-readable storage medium. The computer program 501 is provided for processing by a computer 502, such as control unit 60, for detecting a reflector driving gas (RDG) crossing over a volume reflector 26 in an anesthetic breathing apparatus, such as described above. The computer program comprising code segments, comprising a first code 503 segment for measuring at least one property of a gas stream upstream a fresh gas connection 19 and downstream a reflector unit 26 by means of a gas sensor unit 640, and a second code 504 segment for detecting said reflector driving gas (RDG) crossing over said volume reflector 26 during an inspiration phase, based on said at least one property of said gas stream measured by said gas sensor unit 640.

The computer program may be embodied on a computer-readable medium 500, and/or enable carrying out of the above method.

The present invention has been described above with reference to specific embodiments. However, other embodiments than the above described are equally possible within the scope of the invention. Different ways of delivering RDG may be implemented than those illustrated and described. Various ways of controlling a ratio between RDG and fresh gas are described in patent application PCT/EP2007/062228, which published as WO 2009/062540 A1 and corresponding U.S. Patent Application Publication No. US 2011/0000488 A1, of the same applicant as the present application, which disclosures are hereby incorporated by reference in their entirety by reference for all purposes. Controlling a desired composition of inspiratory gas delivered is provided by the information provided by gas sensor unit 640 facilitating suitable feedback control of the composition. Different method steps than those described above, performing the method by hardware or software, may be

I claim as my invention:

1. A system for detecting breathing circuit leakage in a volume reflector anesthesia breathing circuit, the system comprising: a control computer, a gas sensor unit that is adapted to measure one or more properties of a gas or gas stream, and a volume reflector unit in a common line with the gas sensor unit, the common line conveying a bidirectional flow between a ventilator and a patient circle system, wherein the volume reflector unit comprises a volume reflector having a convoluted tube defining a volume for forming a gas pillar from one or more of a driving gas and an exhaled gas, and the common line interfacing the ventilator in a proximal end and the patient circle system in a distal end, said control computer configured to calculate a leakage volume based on at least one property of the one or more properties of the gas or gas stream measured by the gas sensor unit in the volume reflector anesthesia breathing circuit and to generate and emit an electrical signal representing the calculated leakage volume.

2. The system according to claim 1, wherein the gas sensor unit is connected to the patient circle system and to the volume reflector in the breathing circuit.

3. The system according to claim 1, wherein the control computer is configured to calculate said leakage volume based on the volume of the gas stream measured by the gas sensor unit.

4. The system according to claim 3, wherein the control computer is configured to calculate said leakage volume based on a difference of an inspiratory gas volume measured by the gas sensor unit comprising a volume leaving the volume reflector during inspiration and a volume entering the volume reflector during the preceding expiration.

5. The system according to claim 3, wherein the control computer is configured to provide, dependent on the calculated leakage volume, an indication or warning that a reflector driving gas is crossing over the volume reflector.

6. The system according to claim 1, wherein the control computer is configured to provide information related to leakage volume in said electrical signal.

7. The system according to claim 1, wherein the gas sensor unit is a gas sensor that measures absolute or relative concentration of at least one specific gas component.

8. The system according to claim 1, wherein the gas sensor unit is connected to the volume reflector in the breathing circuit, and wherein the gas sensor unit is configured to measure the property of gas flow at a measurement position thereof, said gas flow measurement being unidirectional or dependent on at least one of a direction of the gas flow out of the volume reflector and into the volume reflector.

9. The system according to claim 8, wherein the gas sensor unit is a gas flow sensor arranged to measure differential pressure drop over a defined distance in a gas line at a measurement position.

10. The system according to claim 1, wherein the gas sensor unit is an ultrasonic gas flow sensor that makes time of flight measurements to provide a signal for gas flow measurements, and measured ultrasonic sound propagation speed, at zero flow, as a measure of gas concentration or gas presence detection.

11. The system according to claim 10, wherein the gas sensor unit is configured to measure a molecular weight of gases measured by measuring the ultrasonic sound propagation speed.

12. The system according to claim 1, wherein the gas sensor unit is configured to only detect relative changes of a concentration of a predetermined gas, and to detect relative gas composition changes during an inspiratory phase.

13. The system according to claim 12, wherein the gas sensor unit is connected to the volume reflector in the breathing circuit, and wherein the gas sensor unit is adapted to detect a change in carbon dioxide presence, or an absence of carbon dioxide, as a measure for reflector driving gas crossing the volume reflector.

14. The system according to claim 1, wherein the gas sensor unit is arranged in the anesthetic breathing circuit to measure at least one property of the one or more properties of said gas stream upstream a fresh gas connection and downstream the reflector unit of said anesthetic breathing circuit, and is configured to provide a signal allowing detection of a reflector driving gas crossing over said volume reflector during inspiration based on said at least one property of said gas stream measured by said gas sensor unit.

15. The system according to claim 1, wherein the gas sensor unit is fluidly connected to and arranged upstream of a junction in said breathing circuit where a fresh gas supply branch line joins a circle system.

16. The system according to claim 1, wherein the gas sensor unit is fluidly connected to and arranged downstream of a junction in said breathing circuit where a driving gas line joins the volume reflector.

17. The system according to claim 16, wherein the sensor unit is arranged downstream of the junction where the reflector joins the circle system and downstream of the carbon dioxide absorber unit, but upstream of the junction where the fresh gas supply branch line joins the circle system.

18. The system according to claim 1, wherein the gas sensor unit is connected to the volume reflector in the breathing circuit, and wherein the gas sensor unit is fluidly connected to and arranged upstream of a junction in said breathing where a fresh gas supply branch line joins a circle system, and wherein the gas sensor unit is arranged at a position selected from the group consisting of a position upstream of a carbon dioxide absorber unit and downstream of the volume reflector in the common line, and a position downstream of a junction where the reflector joins the circle system.

19. The system according to claim 18, wherein the gas sensor unit is arranged upstream of the junction where the reflector joins the circle system and is configured to measure flow or concentration related to reflector driving gas detection only during inspiration, and wherein an additional expiratory flow meter measures expiratory flow.

20. The system according to claim 18, wherein the gas sensor unit is arranged to measure at least one property of the one or more properties of said gas stream upstream of said fresh gas connection or upstream of said junction where the fresh gas supply branch line joins the circle system, and downstream said volume reflector, wherein the property of said gas stream is directly or indirectly related to the composition of said gas.

21. The system according to claim 20, wherein the gas sensor unit is configured to analyze the gas composition present between the volume reflector and an inspiratory limb of the anesthetic breathing circuit.

22. The system according to claim 1, wherein the control computer is configured to set operational modes of an anesthetic breathing apparatus that comprises said breathing circuit, for controlling admixture of reflector driving gas into a patient circle system of said anesthetic breathing circuit.

23. The system according to claim 1, wherein the sensor unit is a unit selected from the group consisting of a gas identification unit, a gas concentration measurement unit, and a gas flow measurement unit.

24. The system according to claim 1, wherein the gas sensor unit is configured to measure a physical property that designates a presence or absence of a gas, directly or indirectly.

25. The system according to claim 24, wherein the gas sensor unit is configured to measure at least one of heat conductivity of said gas, light absorption of said gas, paramagnetic properties of said gas, sound propagation speed in said gas, density of said gas, Doppler shift of a sound wave in said gas, and molecular weight of said gas.

26. The system according to claim 24, wherein the gas sensor unit is configured to measure at least one of a flow of said gas as property of said gas stream; a gas flow-related property of said gas stream, and flow rate or gas volume displaced during a time period calculated from the gas flow.

27. The system according to claim 1, wherein the volume reflector includes an adsorption material that adsorbs anesthetic agent in gas moving in the volume reflector.

28. The system according to claim 1, wherein the volume reflector has a volume of approximately one liter.

29. The system according to claim 1, wherein the convoluted tube is a folded tube.

30. A method for detecting breathing circuit leakage in a patient circle system in an anesthetic breathing apparatus, the method comprising the steps of:
  measuring at least one property of a gas stream with a gas sensor unit; and
  conveying a bidirectional flow in a common line between a ventilator and the patient circle system, wherein a volume reflector unit is disposed in the common line with the gas sensor unit, and the volume reflector unit comprises a volume reflector having a convoluted tube defining a volume for forming a gas pillar from one or more of a driving gas and an exhaled gas, and, based on the at least one property of the gas stream measured by the gas sensor unit, calculating a leakage volume of exhaled gas, wherein the common line interfaces the ventilator in a proximal end and the patient circle system in a distal end.

31. The method according to claim 30, comprising measuring the at least one property of the gas stream upstream a fresh gas connection and downstream the volume reflector of the anesthetic breathing apparatus.

32. The method according to claim 30, wherein the volume reflector includes an adsorption material that adsorbs anesthetic agent in gas moving in the volume reflector.

33. A non-transitory, computer-readable storage medium encoded with programming instructions for detecting breathing circuit leakage in a patient circle system in an anesthetic breathing apparatus, said storage medium loaded into a computer and said programming instructions causing said computer to:
  receive a measurement of at least one property of a gas stream measured by a gas sensor unit;
  detect, based on the at least one property of the gas stream measured by the gas sensor unit, a reflector driving gas crossing over a volume reflector in a common line with the gas sensor unit during an inspiration phase, wherein a volume reflector unit is disposed in the common line with the gas sensor unit, and the volume reflector unit comprises the volume reflector which has a convoluted tube defining a volume for forming a gas pillar from one or more of the reflector driving gas and an exhaled gas, and the common line conveys a bidirectional flow between a ventilator and the patient circle system and the common line interfaces the ventilator in a proximal end and the patient circle system in a distal end; and
  calculate a leakage volume of an exhaled gas based on the at least one property of the gas stream measured by the gas sensor unit.

34. A system for detecting breathing circuit leakage in a volume reflector anesthesia breathing circuit, the system comprising: a control computer, a gas sensor unit that is adapted to measure one or more properties of a gas or gas stream, and a volume reflector unit in a common line with the gas sensor unit, wherein the volume reflector unit comprises a volume reflector having a convoluted tube defining a volume for forming a gas pillar from one or more of a driving gas and an exhaled gas, wherein the volume reflector has a volume of approximately one liter, and the common line interfacing a ventilator in a proximal end and the volume reflector anesthesia breathing circuit in a distal end, the control computer configured to calculate a leakage volume based on at least one property of the one or more properties of the gas or gas stream measured by the gas sensor unit in the volume reflector anesthesia breathing circuit and to generate and emit an electrical signal representing the calculated leakage volume.

* * * * *